United States Patent [19]

Bielefeldt et al.

[11] Patent Number: 5,210,340
[45] Date of Patent: May 11, 1993

[54] PREPARATION OF POLYFLUOROBUTENES

[75] Inventors: Dietmar Bielefeldt, Ratingen; Albrecht Marhold, Leverkusen, both of Fed. Rep. of Germany

[73] Assignee: Bayer Aktiengesellschaft, Leverkusen, Fed. Rep. of Germany

[21] Appl. No.: 866,930

[22] Filed: Apr. 10, 1992

Related U.S. Application Data

[60] Division of Ser. No. 824,691, Jan. 21, 1992, Pat. No. 5,146,019, which is a continuation of Ser. No. 529,770, May 30, 1990, abandoned, which is a continuation of Ser. No. 405,101, Sep. 8, 1989, abandoned, which is a continuation of Ser. No. 218,735, Jul. 13, 1988, abandoned.

[30] Foreign Application Priority Data

Jul. 30, 1987 [DE] Fed. Rep. of Germany ....... 3725213

[51] Int. Cl.$^5$ .............................................. C07C 17/20
[52] U.S. Cl. .................................................... 570/160
[58] Field of Search ........................ 570/167, 168, 160

[56] References Cited

U.S. PATENT DOCUMENTS

| | | | |
|---|---|---|---|
| 2,830,100 | 4/1958 | Swemer | 570/167 |
| 4,374,289 | 2/1983 | Van Der Puy | 570/168 |
| 4,792,643 | 12/1988 | Sobolev | 570/168 |

Primary Examiner—Alan Siegel
Attorney, Agent, or Firm—Sprung, Horn, Kramer & Woods

[57] ABSTRACT

1,1,1,2,4,4,4-Heptafluoro-2-butene and 2-chloro-1,1,1,4,4,4-hexafluoro-2-butene 1,V5VjV9are prepared simultaneously by reacting hexachlorobutadiene with hydrogen fluoride with the addition of catalytic amounts of titanium halide, antimony trihalide and/or antimony pentahalide.

6 Claims, No Drawings

PREPARATION OF POLYFLUOROBUTENES

This is a division of application Ser. No. 824,691, filed Jan. 21, 1992, now U.S. Pat. No. 5,146,019, which is a continuation of Ser. No. 529,770, filed May 30, 1990, now abandoned which is a continuation of Ser. No. 405,101, filed Sep. 8, 1989, now abandoned, which is a continuation of Ser. No. 218,735, filed Jul. 13, 1988, now abandoned.

The present invention relates to a process for the simultaneous preparation of 2-chloro-1,1,1,4,4,4-hexafluoro-2-butene and 1,1,1,2,4,4,4-heptafluoro-2-butene from hexachlorobutadiene.

1,1,1,2,4,4,4-Heptafluoro-2-butene, also called heptafluorobutene hereinafter, is a known intermediate for preparing chlorofluorobutane, which is a stable heat transfer agent, and also trifluoroacetic acid and pentafluoropropionic acid (see U.S. Pat. No.3,287,425). It is known to prepare heptafluorobutene by reacting hexachlorobutadiene with an alkali metal fluoride in a solvent, for example dimethyl sulphoxide (see U.S. Pat. No. 3,287,425). The disadvantage of this process is the use of a solvent and the formation of alkali metal chlorides, which must be separated off and disposed of in a costly manner.

2-Chloro-1,1,1,4,4,4-hexafluoro-2-butene, also called chlorohexafluorobutene hereinafter, is a known intermediate for preparing sodium trifluoroacetate. It is known that it can be prepared by reacting hexachlorobutadiene with hydrogen fluoride and elemental chlorine with the addition of antimony pentachloride. The yields of 5 to 10% are very low since 2,3-dichloro-1,1,1,4,4,4-hexafluoro-2-butene is obtained as the main product (see U.S. Pat. No. 2,554,857 and C.A. 46, 7987 i to 7988 a). Impure chlorohexafluorobutene can also be obtained as a side product, when perfluoro-2-butine is prepared from 2,3-dichloro-1,1,1,4,4,4-hexafluoro-2-butene in a 10-day reaction by reduction with zinc (see J. A. C. S. 71, 298 (1949)). These methods are unsuitable for an industrial preparation of chlorohexafluorobutene. Their disadvantages are in particular the use of elemental chlorine or zinc and the low yields of a product which is not yet purified.

There has now been found a process for the simultaneous preparation of 1,1,1,2,4,4,4-heptafluoro-2-butene and 2-chloro-1,1,1,4,4,4-hexafluoro-2-butene, characterized in that hexachlorobutadiene is reacted with hydrogen fluoride with the addition of catalytic amounts of a titanium halide, antimony trihalide and/or antimony pentahalide.

The hexachlorobutadiene which is required as a starting material for carrying out the process according to the invention can be obtained commercially, for example from Aldrich Chemie Co., Steinheim, and can be used in its commercial purity. The second starting material required, hydrogen fluoride, is preferably used in anhydrous form and can also be obtained commercially in this form.

Hydrogen fluoride can be used for example in amounts of 5 to 100 moles per mole of hexachlorobutadiene. Preferably this amount is 10 to 50 moles per mole of hexachlorobutadiene.

In the process according to the invention, titanium tetrahalide, antimony trihalide and/or antimony pentahalide are added in catalytic amounts. This amount can be for example 0.1 to 30 mole %, relative to hexachlorobutadiene. Preferably this amount is 1 to 25 mole %.

Examples of suitable halides are fluorides and chlorides, in particular titanium tetrachloride, antimony trifluoride, antimony pentafluoride, antimony pentachloride and mixed antimony pentahalides of the empirical formula $SbCl_nF_{5-n}$ with n=0.1 to 4.9. Particular preference is given to the addition of antimony pentachloride. Mixtures of various halides can also be used.

The process according to the invention can be carried out at different temperatures, for example within the range of $-20°$ to $+200°$ C. In general it is advantageous to start the reaction at low temperatures, for example at $-10°$ to $+18°$ C., and complete it at higher temperatures, for example at 40° to 160° C. Since at atmospheric pressure hydrogen fluoride boils at about 20° C., it is necessary, if the reaction is carried out at temperatures above about 18° C., to work in closed vessels under the particular autogenous pressure and/or to prevent the evaporation of hydrogen fluoride by pressurizing with another gas, for example nitrogen. The resulting hydrogen chloride can, if necessary, be released through a pressure-maintaining valve.

In general it is advantageous after the completion of the reaction to continue stirring for some time at the final temperature, for example 1 to 5 hours.

The workup of the reaction mixture can be carried out by first separating off any hydrogen fluoride still present, for example by phase separation or distillation, and then subjecting the residue to fractional distillation or pouring the residue which has been freed from hydrogen fluoride onto ice, separating off the resulting organic phase and subjecting it to fractional distillation. If desired, the catalyst can be separated from the residue from which hydrogen fluoride has been removed, for example by extraction with a tartaric acid solution.

In this manner, heptafluorobutene and chlorohexafluorobetene can be obtained in various ratios relative to each other, and both products can be isolated in very pure form. Generally the crude reaction mixture contains more chlorohexafluorobutene than heptafluorobutene.

It is particularly surprising that by using the method according to the invention, it is so advantageously possible to obtain heptafluorobutene using hydrogen fluoride and no solvent and chlorohexafluorobutene without using elemental chlorine.

EXAMPLES

EXAMPLE 1

1400 ml of hexachlorobutadiene were added at 0° C. to 4.5 l of hydrogen fluoride to which 74 ml of antimony pentachloride had been added. After the evolution of hydrogen chloride had ceased, 25 bar of nitrogen were injected, and the temperature was increased to 120° C. The mixture was stirred for 2 hours at this temperature, and the hydrogen chloride formed was released through a pressure-maintaining valve. Unconverted hydrogen fluoride was then distilled off and the residue was poured onto ice, which was followed by fractional distillation to give: 790 g (65% of theory) of 2-chloro-1,1,1,4,4,4-hexafluoro-2-butene of a boiling point of 36° C. at 1 bar and 20 g (2% of theory) of 1,1,1,2,4,4,4-heptafluoro-2-butene of a boiling point of 9° C. at 1 bar.

In addition, 620 g of unconverted hexachlorobutadiene were recovered.

The isolated substances were characterized by nuclear magnetic resonance spectra and mass spectra.

EXAMPLE 2

720 ml of hexachlorobutadiene were added at −4° C. to 3 l of hydrogen fluoride and 50 ml of antimony pentachloride. The reaction mixture was slowly warmed to 17° C. After the evolution of hydrogen chloride had ceased, 30 bar of nitrogen were injected, the mixture was stirred for 3 hours at 140° C. and the hydrogen chloride formed was released through a pressure-maintaining valve. The mixture of products was then cooled and purified by distillation to give: 198 g (=23.5% of theory) of 1,1,1,2,4,4,4-heptafluoro-2-butene and 521 g (=56.6% of theory) of 2-chloro-1,1,1,4,4,4-hexafluoro-2-butene.

Boiling points and characterization were as given in Example 1. In addition, 20 g of unconverted hexachlorobutadiene were recovered.

EXAMPLE 3

720 ml of hexachlorobutadiene were added at −2° C. to 3 l of hydrogen fluoride to which had been added 150 ml of antimony pentachloride and 50 g of antimony trifluoride. This mixture was kept at 20° C. for 6.5 hours. 25 bar of nitrogen were then injected, and the temperature was increased to 138° C. The mixture was stirred for 4.5 hours at this temperature, and the hydrogen chloride formed was released through a pressure-maintaining valve. Unconverted hydrogen fluoride was separated off, and the residue was subjected to fractional distillation to give: 340 g (=42% of theory) of 1,1,1,2,4,4,4-heptafluoro-2-butene and 485 g (=54% of theory) of 2-chloro-1,1,1,4,4,4-hexafluoro-2-butene.

Boiling points and characterization were as given in Example 1. In addition, 40 g of unconverted hexachlorobutadiene were recovered.

What is claimed is:

1. A process for the simultaneous preparation of 1,1,1,2,4,4,4-heptafluoro-2-butene and 2-chloro-1,1,1,4,4,4-hexafluoro-2-butene, in which hexachlorobutadiene is reacted with hydrogen fluoride with the addition of catalytic amounts of a titanium tetrahalide in the absence of elemental chlorine.

2. A process according to claim 1, in which 5 to 100 moles of hydrogen fluoride are used per mole of hexachlorobutadiene.

3. A process according to claim 1, in which 0.1 to 30 mole % of the titanium tetra halide, relative to hexachlorobutadiene, is used.

4. A process according to claim 1, which is carried out at a temperature in the range of −20° C. to +200° C.

5. A process according to claim 4, which at a temperature above 18° C. is carried out in a closed vessel and/or by pressurizing another gas.

6. A process according to claim 1, in which any hydrogen fluoride still present after the reaction is first removed from the reaction mixture and the residue is then subjected to fractional distillation.

* * * * *